US00PP18077P2

(12) United States Plant Patent
Schräder

(10) Patent No.: US PP18,077 P2
(45) Date of Patent: Sep. 25, 2007

(54) ***OSTEOSPERMUM* PLANT NAMED 'SUMIPAS 01'**

(50) Latin Name: *Osteospermum ecklonis*
Varietal Denomination: Sumipas 01

(76) Inventor: Ralf Schräder, Karl-Leusner-Str. 15, D-59348 Lüdinghausen (DE)

( * ) Notice: Subject to any disclaimer, the term of this patent is extended or adjusted under 35 U.S.C. 154(b) by 0 days.

(21) Appl. No.: 11/323,153

(22) Filed: Dec. 30, 2005

(51) Int. Cl.
*A01H 5/00* (2006.01)

(52) U.S. Cl. ..... Plt./360
(58) Field of Classification Search ..... Plt./360
See application file for complete search history.

(56) References Cited

PUBLICATIONS

Upov CD–Rom Plant Variety Database 2006/04 for cultivar Sumipas 01.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Osteospermum* plant named 'Sumipas 01', characterized by its upright, outwardly spreading, compact and mounded plant habit; freely branching habit; freely, early and continuous flowering habit; and inflorescences with light purple-colored ray florets.

1 Drawing Sheet

Botanical designation: *Osteospermum ecklonis.*
Botanical denomination: 'Sumipas 01'.

BACKGROUND OF THE INVENTION

The present Invention relates to a new and distinct cultivar of *Osteospermum* plant, botanically known as *Osteospermum ecklonis,* and hereinafter referred to by the name 'Sumipas 01'.

The new *Osteospermum* is a product of a planned breeding program conducted by the Inventor in Lüdinghausen, Germany. The objective of the breeding program was to create new compact and early flowering *Osteospermum* cultivars with large and attractive inflorescences.

The new *Osteospermum* originated from a cross-pollination in April, 2001 of a proprietary *Osteospermum ecklonis* selection identified as code number 24, not patented, as the female, or seed, parent with the *Osteospermum ecklonis* cultivar Sumlight, not patented, as the male, or pollen, parent. The new *Osteospermum* was discovered and selected by the Inventor as a single flowering plant within the progeny of the stated cross-pollination grown in a controlled environment in Lüdinghausen, Germany in April, 2002.

Asexual reproduction of the new *Osteospermum* by terminal vegetative cuttings was first conducted in L üdinghausen, Germany in May, 2002. Asexual reproduction by cuttings has shown that the unique features of this new *Osteospermum* are stable and reproduced true to type in successive generations.

SUMMARY OF THE INVENTION

The cultivar 'Sumipas 01' has not been observed under all possible environmental conditions. The phenotype may vary somewhat with variations in environment such as temperature and light intensity without, however, any variance in genotype.

The following traits have been repeatedly observed and are determined to be the unique characteristics of 'Sumipas 01'. These characteristics in combination distinguish 'Sumipas 01' as a new and distinct *Osteospermum:*

1. Upright, outwardly spreading, compact and mounded plant habit.
2. Freely branching habit.
3. Freely, early and continuous flowering habit.
4. Inflorescences with light purple-colored ray florets.

Plants of the new *Osteospermum* differ primarily from plants of the female parent selection in flowering time as plants of the new *Osteospermum* flower about 10 days earlier than plants of the female parent selection. Plants of the new *Osteospermum* differ primarily from plants of the male parent, the cultivar Sumlight in plant size as plants of the new *Osteospermum* are more compact than plants of the cultivar Sumlight.

Plants of the new *Osteospermum* can be compared to plants of the cultivar Osjotis, disclosed in U.S. Plant Pat. No. 15,577. In side-by-side comparisons, plants of the new *Osteospermum* differed from plants of the cultivar Osjotis in the following characteristics:

1. Plants of the new *Osteospermum* were larger than plants of the cultivar Osjotis.
2. Plants of the new *Osteospermum* had thicker stems than plants of the cultivar Osjotis.
3. Plants of the new *Osteospermum* had larger leaves than plants of the cultivar Osjotis.
4. Plants of the new *Osteospermum* were more freely flowering than plants of the cultivar Osjotis.
5. Plants of the new *Osteospermum* and the cultivar Osjotis differed in ray floret coloration.

BRIEF DESCRIPTION OF THE PHOTOGRAPH

The accompanying colored photograph illustrates the overall appearance of the new *Osteospermum* showing the colors as true as it is reasonably possible to obtain in colored reproductions of this type. Colors in the photograph may differ from the color values cited in the detailed botanical description which accurately describe the colors of the new *Osteospermum*. The photograph comprises a side perspective view of a typical flowering plant of 'Sumipas 01' grown in a container.

DETAILED BOTANICAL DESCRIPTION

The new *Osteospermum* has not been observed under all possible environmental conditions. The phenotype may vary somewhat with variations in environment such as temperature and light intensity, without, however, any variance in genotype.

The aforementioned photograph, following observations and measurements describe plants grown in Lüdinghausen, Germany in an outdoor nursery during the spring and summer and under commercial production practices. Plants were about three months from planting rooted young plants when the photograph and description were taken. During the production of the plants, day temperatures ranged from 16° C. to 30° C. and night temperatures ranged from 8° C. to 14° C. In the following description, color references are made to The Royal Horticultural Society Colour Chart, 2001 Edition, except where general terms of ordinary dictionary significance are used.

Botanical classification: *Osteospermum ecklonis* cultivar 'Sumipas 01'.

Parentage:

*Female, or seed, parent.*—Proprietary selection of *Osteospermum ecklonis* identified as code number 24, not patented.

*Male, or pollen, parent.*—*Osteospermum ecklonis* cultivar Sumlight, not patented.

Propagation:

*Type.*—Terminal vegetative cuttings.

*Time to initiate rooting, summer.*—About 14 days at 16° C.

*Time to initiate rooting, winter.*—About 18 days at 16° C.

*Time to produce a rooted young plant, summer.*—About 30 days at 16° C.

*Time to produce a rooted young plant, winter.*—About 32 days at 16° C.

*Root description.*—Fine, fibrous; color, 162C.

*Rooting habit.*—Freely branching; moderately dense.

Plant description:

*Plant form and growth habit.*—Perennial herbaceous container and garden plant. Upright, somewhat outwardly spreading, compact and mounded plant habit; broad inverted triangle. Freely branching habit, about 14 primary lateral branches and numerous secondary lateral branches.

*Plant height.*—About 25 cm.

*Plant width or area of spread.*—About 20 cm to 25 cm.

*Lateral branches.*—Length: About 20 cm. Diameter: About 5 mm. Internode length: About 6 cm to 8 cm. Aspect: Upright and outwardly spreading. Strength: Strong. Texture: Smooth, glabrous. Color: 145B.

*Foliage description.*—Arrangement: Alternate; simple. Length: About 3.5 cm to 4 cm. Width: About 2.5 cm to 2.8 cm. Shape: Lanceolate. Apex: Emarginate. Base: Acute to truncate. Margin: Slightly serrate. Venation pattern: Pinnate. Texture, upper and lower surfaces: Smooth, glabrous. Color: Developing foliage, upper surface: 146A. Developing foliage, lower surface: 146B. Fully expanded foliage, upper surface: 147A; venation, 144A. Fully expanded foliage, lower surface: 144A; venation, 144A. Petiole: Length: About 1 cm to 1.5 cm. Diameter: About 2 mm to 3 mm. Texture, upper and lower surfaces: Glabrous, smooth. Color, upper surface: 144A. Color, lower surface: 144B.

Inflorescence description:

*Appearance.*—Solitary terminal and axillary inflorescences held above and beyond the foliage on strong peduncles. Composite inflorescence form, radially symmetrical, with elliptic to ligulate-shaped ray florets and disc florets massed at the center; ray and disc florets develop acropetally on a capitulum. Inflorescences not persistent. Inflorescences face mostly upright to outwardly.

*Flowering response.*—Plants flower continuous and freely from the early spring through the fall in Germany. Early flowering habit; plants grown in containers begin flowering about six to eight weeks after pinching.

*Postproduction longevity.*—Inflorescences maintain good color and substance for about four to six days on the plant.

*Quantity of inflorescences.*—Freely flowering; at one time, about eight to twelve open inflorescences and inflorescence buds per lateral stem.

*Fragrance.*—Faint.

*Inflorescence bud.*—Length: About 2 cm. Diameter: About 1 cm. Shape: Ovoid. Color: N144A.

*Inflorescence size.*—Diameter: About 6 cm to 6.5 cm. Depth (height): About 5 cm. Disc diameter: About 2 cm.

*Ray florets.*—Length: About 2.7 cm to 3 cm. Width: About 8 mm to 10 mm. Shape: Elliptic to ligulate. Apex: Obtuse. Base: Attenuate. Margin: Entire. Texture, upper and lower surfaces: Smooth, glabrous. Number of ray florets per inflorescence: About 16 to 20 in a single whorl. Color: When opening, upper surface: N74B to N74C. When opening, lower surface: Alternating longitudinal stripes of N88A and 177B. Fully opened, upper surface: N74C; mid-section and towards the base, 76C; at the base, 79A; color becoming closer to 84B with development. Fully opened, lower surface: Alternating longitudinal stripes of 86C and 165B.

*Disc florets.*—Shape: Tubular, elongated. Apex: Five-pointed. Length: About 1 cm. Width: At apex: About 5 mm. At base: About 1 mm. Number of disc florets per inflorescence: About 60. Color: N89A.

*Phyllaries.*—Length: About 1.5 mm to 2 mm. Diameter: About 1 mm. Shape: Lanceolate. Apex: Acute. Base: Truncate. Margin: Entire. Texture, upper and lower surfaces: Smooth, glabrous. Number per inflorescence: About 16 to 20. Color, upper and lower surfaces: 137C.

*Peduncles.*—Length: About 5 cm to 7 cm. Diameter: About 1 mm. Angle: Terminal peduncles, mostly upright; axillary peduncles about 35° to 45° from stem axis. Strength: Strong. Texture: Smooth, glabrous. Color: 144A.

*Reproductive organs.*—Androecium: Present on disc florets only. Stamen number: Five per floret; fused around style. Anther shape: Oblong. Anther length: Less than 0.5 mm. Anther color: 25B. Pollen amount: Scarce. Pollen color: 25B. Gynoecium:

Present on both ray and disc florets. Pistil number: One per floret. Pistil length: About 4 mm. Stigma shape: Two-parted. Stigma color: N81A. Style length: About 1 mm. Style color: 144C. Ovary color: 144C.

*Seeds.*—Length: About 3 mm. Diameter: About 1.5 mm. Color: 200D.

Disease/pest resistance: Resistance to pathogens and pests common to *Osteospermums* has not been observed on plants grown under commercial greenhouse or outdoor conditions.

Temperature tolerance: Plants of the new *Osteospermum* have been observed to tolerate temperatures from 0° C. to 40° C.

It is claimed:

1. A new and distinct cultivar of *Osteospermum* plant named 'Sumipas 01', as illustrated and described.

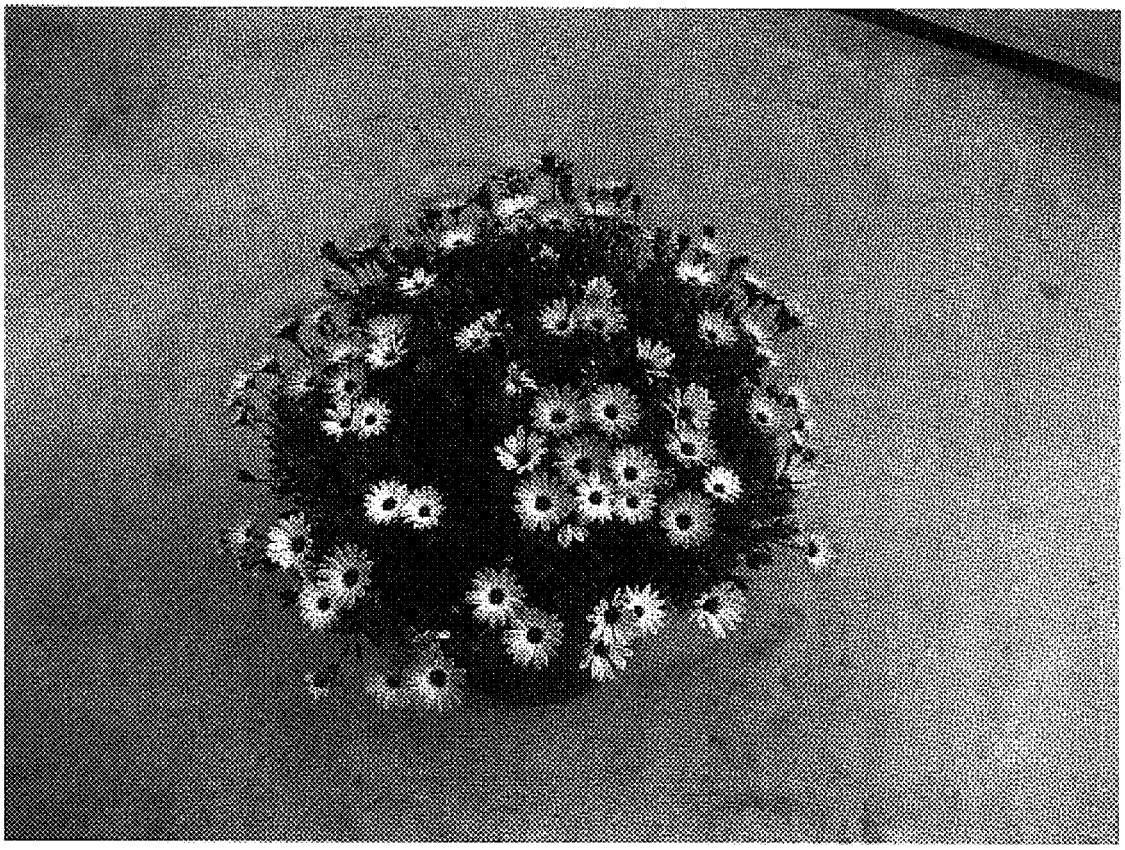

* * * * *